(12) United States Patent
Gerner et al.

(10) Patent No.: US 7,259,840 B1
(45) Date of Patent: Aug. 21, 2007

(54) FLUID ANALYSIS APPARATUS

(75) Inventors: Yuri Gerner, Mendota Heights, MN (US); Carl W. Sims, St. Paul, MN (US); Jonathan Thompson, Center City, MN (US)

(73) Assignee: Systec, LLC, New Brighton, MN (US)

( * ) Notice: Subject to any disclaimer, the term of this patent is extended or adjusted under 35 U.S.C. 154(b) by 337 days.

(21) Appl. No.: 11/051,767

(22) Filed: Feb. 4, 2005

Related U.S. Application Data

(63) Continuation-in-part of application No. 11/027,456, filed on Dec. 28, 2004.

(51) Int. Cl.
*G01N 1/00* (2006.01)

(52) U.S. Cl. .......................................... 356/36

(58) Field of Classification Search ...................... None
See application file for complete search history.

(56) References Cited

U.S. PATENT DOCUMENTS

| | | |
|---|---|---|
| 3,795,450 A | 3/1974 | Munk |
| 3,954,341 A | 5/1976 | Uffenheimer |
| 4,009,382 A | 2/1977 | Nath |
| 4,260,257 A | 4/1981 | Neeley et al. |
| 4,530,569 A | 7/1985 | Squire |
| 4,571,078 A | 2/1986 | Capps, II |
| 4,575,424 A | 3/1986 | Allington et al. |
| 4,754,009 A | 6/1988 | Squire |
| 4,802,768 A | 2/1989 | Gifford et al. |
| 4,816,123 A | 3/1989 | Ogan et al. |
| 4,867,559 A | 9/1989 | Bach |
| 4,886,356 A | 12/1989 | Paradis |
| 4,889,611 A | 12/1989 | Blough, Jr. |
| 4,973,142 A | 11/1990 | Squire |
| 4,975,505 A | 12/1990 | Squire |
| 4,977,025 A | 12/1990 | Squire |
| 4,999,248 A | 3/1991 | Squire |
| 5,000,547 A | 3/1991 | Squire |
| 5,006,382 A | 4/1991 | Squire |
| 5,061,024 A | 10/1991 | Keys |
| 5,076,659 A | 12/1991 | Bekiarian et al. |
| 5,120,129 A | 6/1992 | Farquharson et al. |
| 5,140,169 A | 8/1992 | Evens et al. |
| 5,153,679 A | 10/1992 | Gilby |
| 5,184,192 A | 2/1993 | Gilby et al. |
| 5,267,341 A | 11/1993 | Shearin |
| 5,404,217 A | 4/1995 | Janik et al. |
| 5,416,879 A | 5/1995 | Liu |
| 5,444,807 A | 8/1995 | Liu |
| 5,570,447 A | 10/1996 | Liu |
| 5,604,587 A | 2/1997 | Che et al. |
| 5,608,517 A | 3/1997 | Munk |
| 5,822,067 A | 10/1998 | Yanik |
| 5,847,835 A | 12/1998 | Fukunaga |
| 5,854,863 A | 12/1998 | Erb et al. |

(Continued)

*Primary Examiner*—Tu T. Nguyen
(74) *Attorney, Agent, or Firm*—Haugen Law Firm PLLP

(57) ABSTRACT

A fluid analysis apparatus for containing and analyzing a fluid sample includes a cell body assembly having a plurality of distinct portions in fluid communication with one another and with the distinct portions being hydraulically sealed to one another through the use of one or more resilient gaskets interposed between adjacent ones of the plurality of distinct portions of the cell body assembly. The one or more resilient gaskets enable both hydraulic sealing of adjacent distinct portions, as well as fluid coupling and routing through the fluid analysis apparatus.

5 Claims, 9 Drawing Sheets

U.S. PATENT DOCUMENTS

| | | |
|---|---|---|
| 5,883,721 A | 3/1999 | Gilby et al. |
| 5,917,606 A | 6/1999 | Kaltenbach |
| 6,011,882 A | 1/2000 | Dasgupta et al. |
| 6,016,372 A | 1/2000 | Fein et al. |
| 6,020,207 A | 2/2000 | Liu |
| 6,188,813 B1 | 2/2001 | Dourdeville et al. |
| 6,526,188 B2 | 2/2003 | Dourdeville et al. |
| 6,542,231 B1 | 4/2003 | Garrett |
| 6,678,051 B2 | 1/2004 | Gerner et al. |
| 6,734,961 B2 | 5/2004 | Gerner et al. |
| 6,821,773 B1 * | 11/2004 | Newberg .................. 435/309.2 |
| 6,972,568 B2 * | 12/2005 | Haner et al. ................. 324/321 |
| 2003/0160166 A1 * | 8/2003 | Glish et al. .................. 250/288 |

* cited by examiner

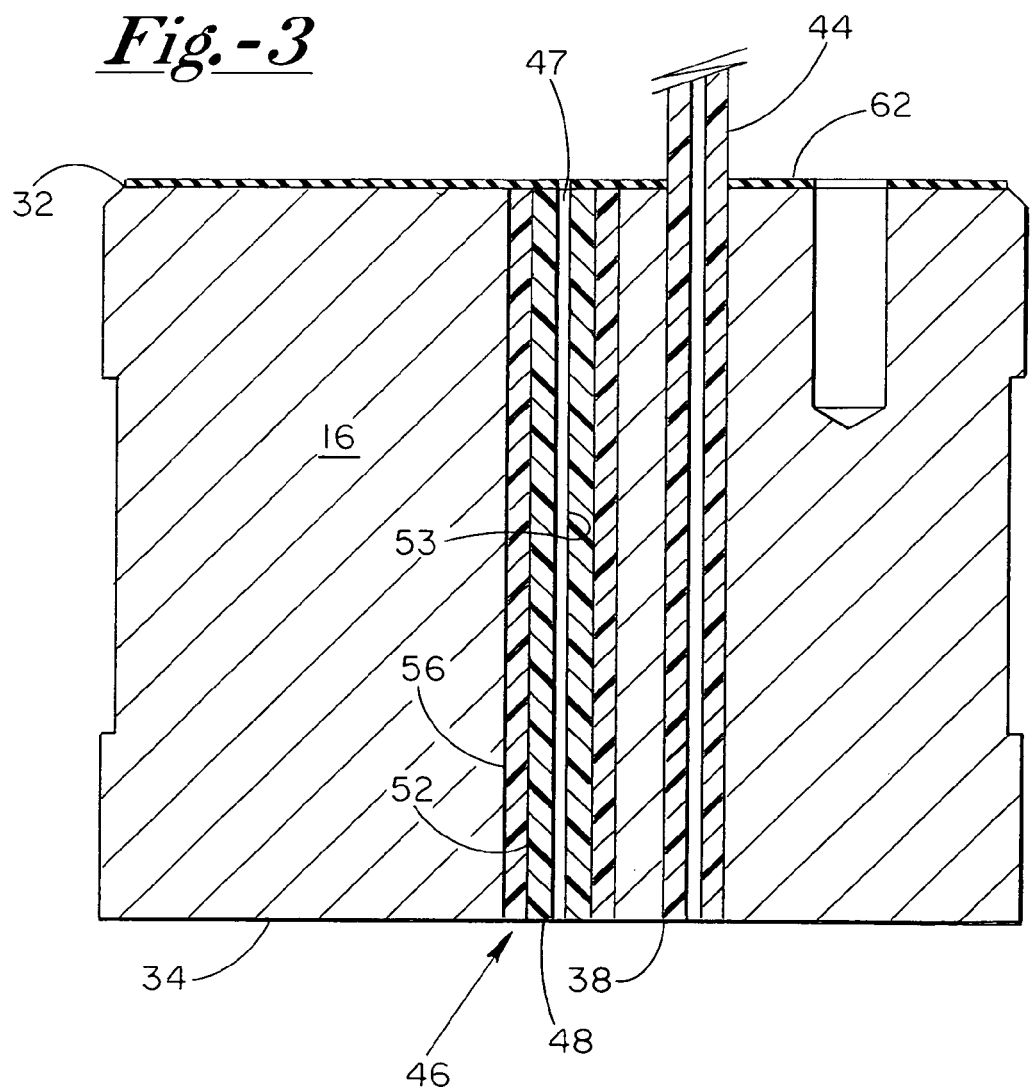

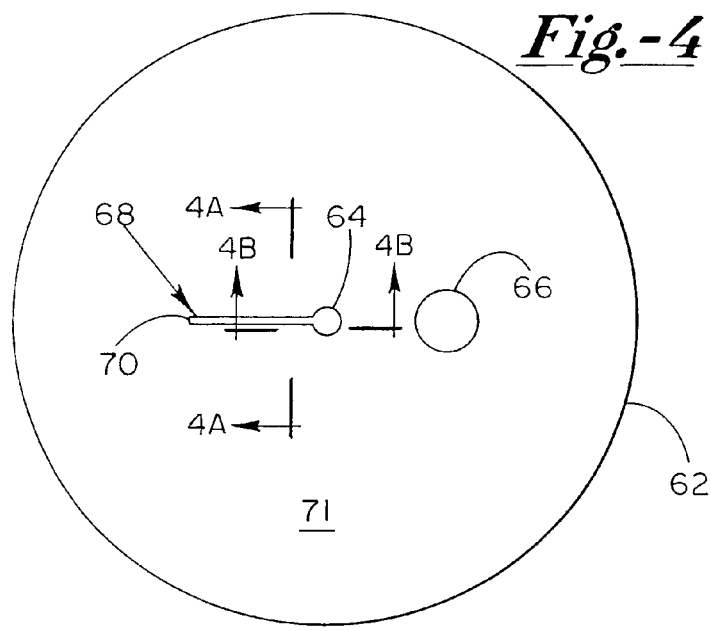
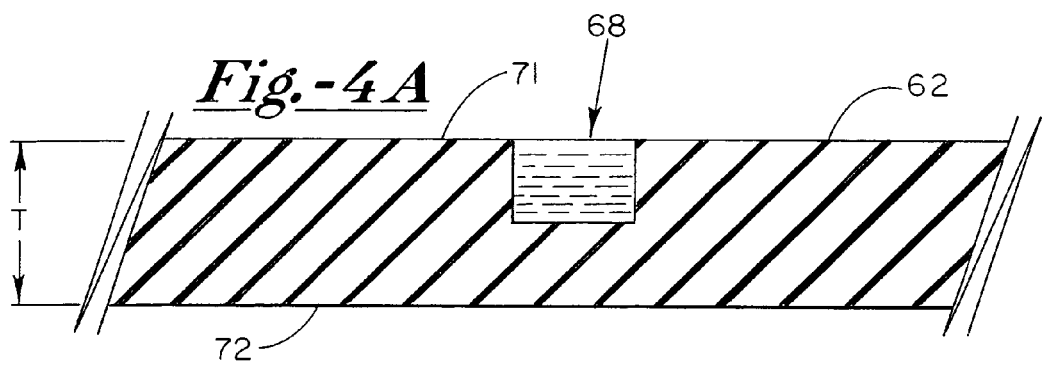
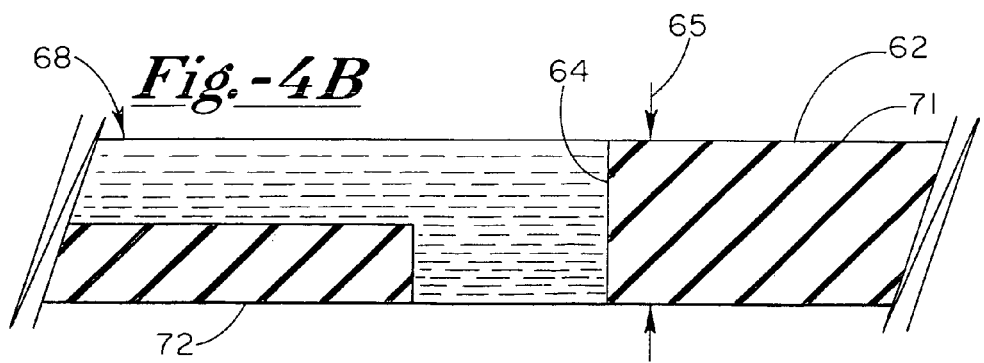

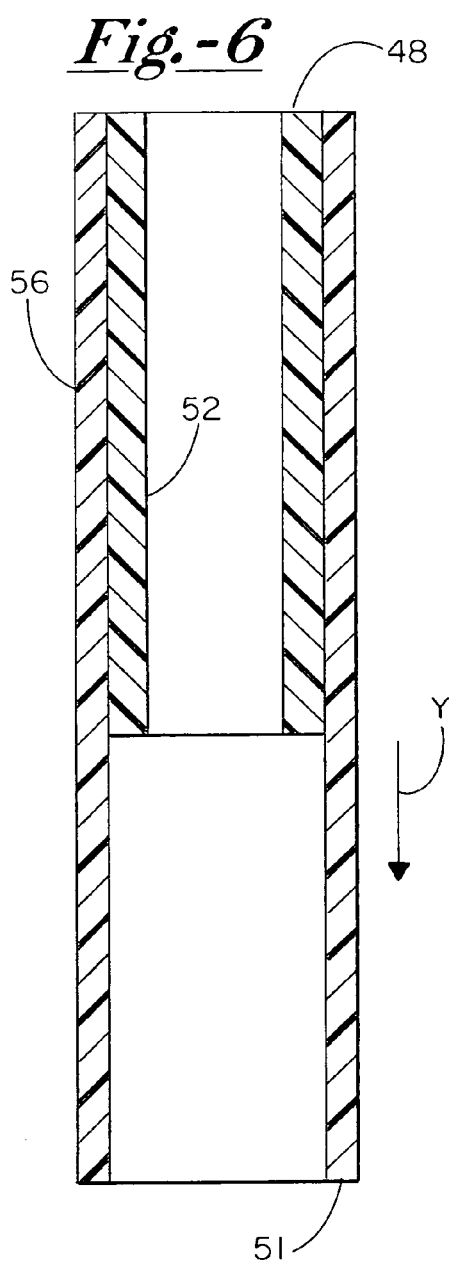
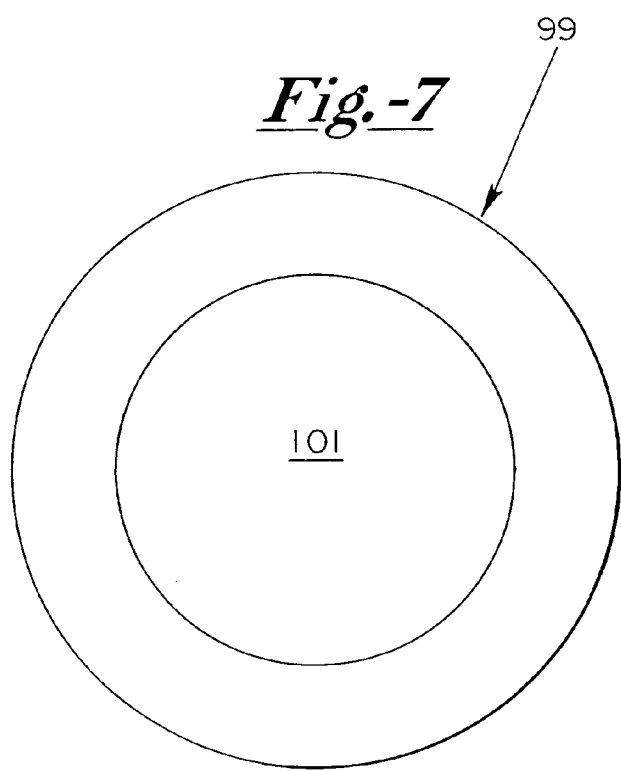

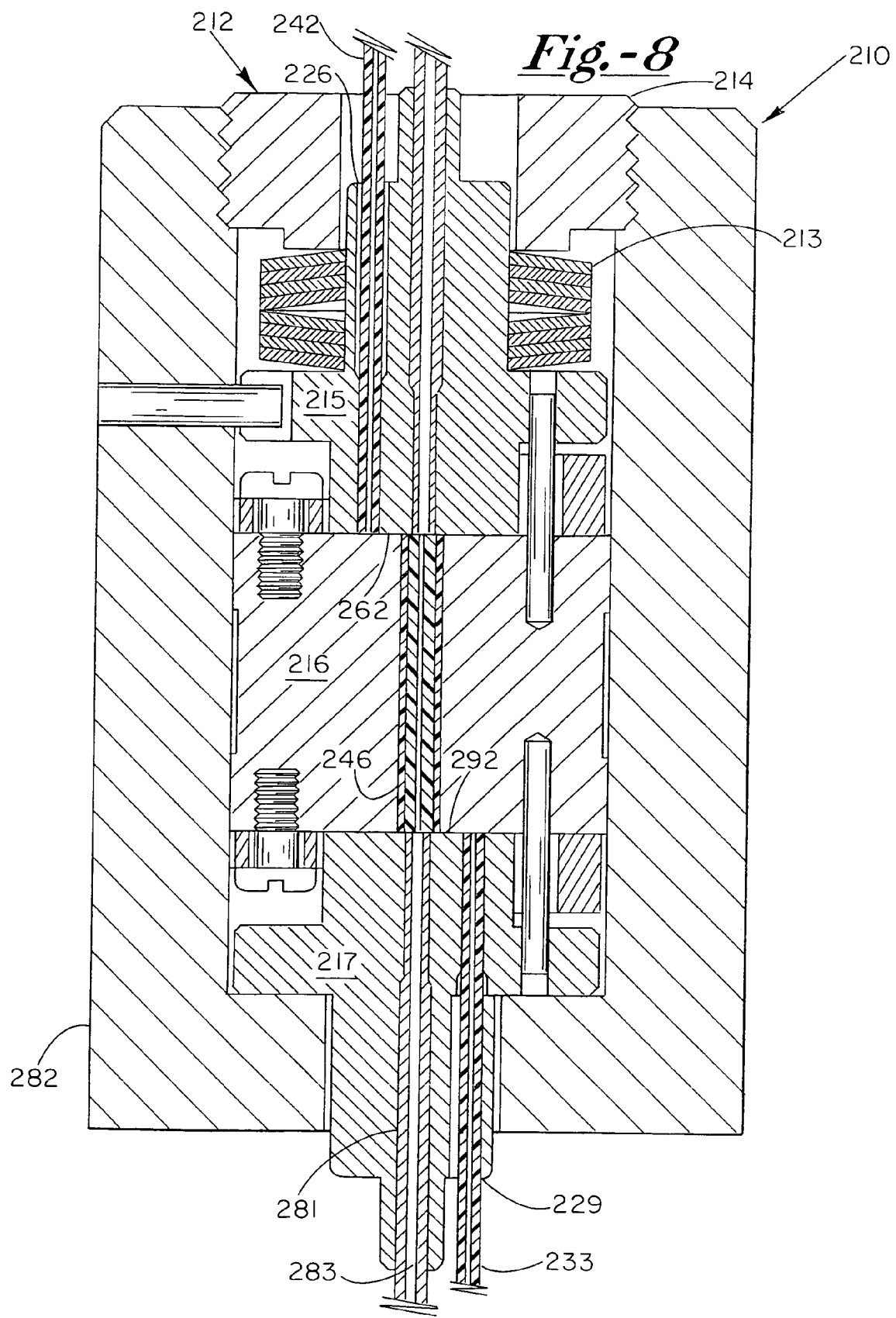

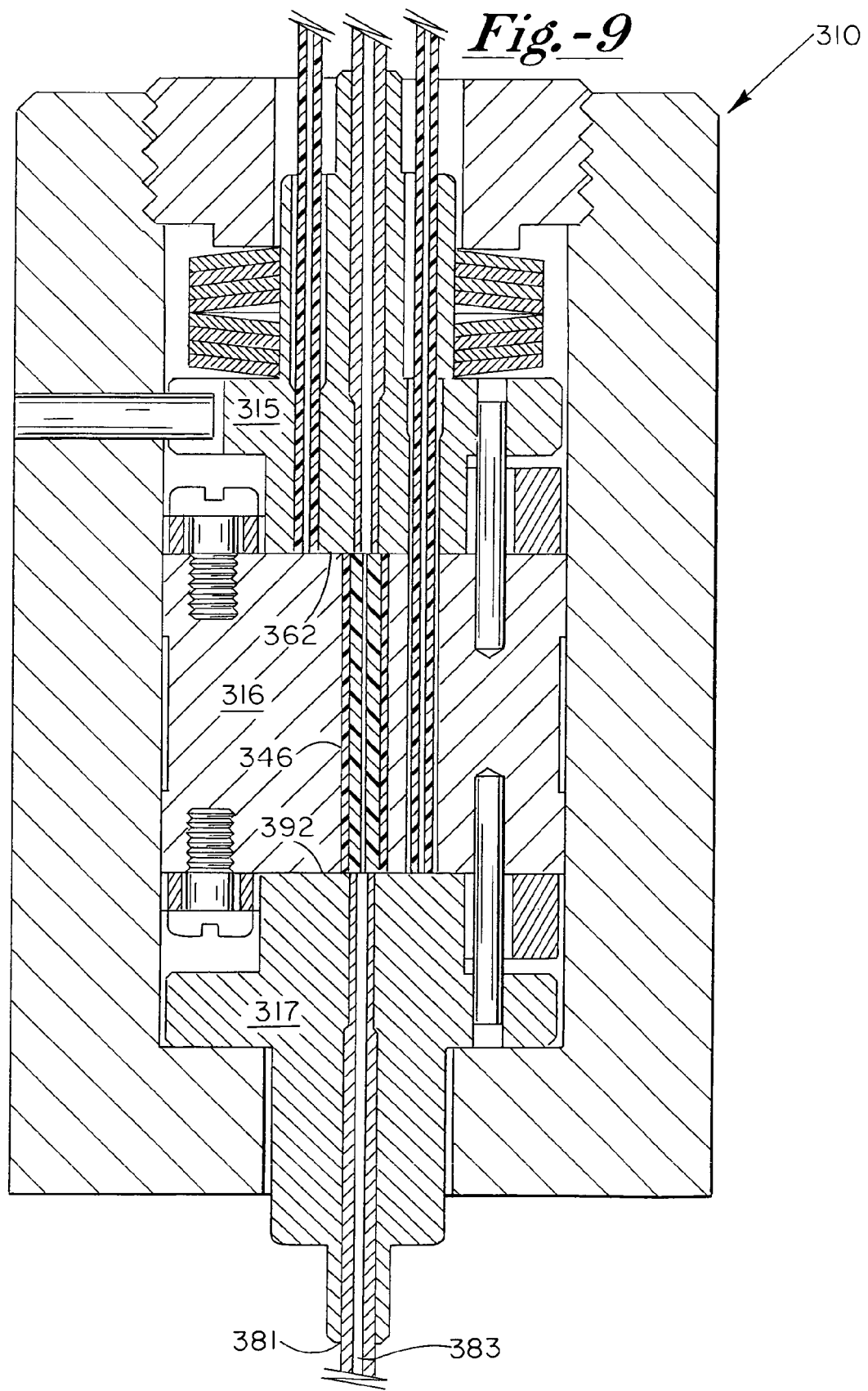

FLUID ANALYSIS APPARATUS

CROSS-REFERENCE TO RELATED APPLICATION

This application is a continuation-in-part of U.S. patent application Ser. No. 11/027,456, filed on Dec. 28, 2004 and entitled FLUID ANALYSIS APPARATUS, the content of which is incorporated herein in its entirety.

FIELD OF THE INVENTION

The present invention relates to fluid analysis assemblies generally, and more particularly to apparatus for analyzing fluids in analytical chemistry applications such as flow cells for use in spectrophotometry. This invention also relates to methods for fabricating such apparatus.

BACKGROUND OF THE INVENTION

A variety of fluid analysis cell assemblies have been designed and implemented for use in analyzing fluid samples, particularly in analytical chemistry applications. Such fluid cell assemblies may be constructed to statically hold a pre-designated volume of fluid to be analyzed, or may instead be configured as a flow cell, which are typically used to transport fluid samples through an analysis chamber.

In flow cell arrangements, fluid samples are typically transported through a chamber disposed between a radiant energy source and a radiant energy detector, which detector measures the relevant radiant energy wavelength absorption or transmission through the fluid sample. An example of such a detector is a spectrophotometer. Various analytical instruments then utilize the absorbed versus transmitted radiant energy to determine the composition of the associated fluid sample.

To efficiently pass the radiant energy through the fluid sample in the analysis chamber, however, the wall defining the fluid-containing chamber is preferably a material having an index of refraction that is less than that of the fluid sample. Such an index of refraction relationship between the fluid sample and the analysis chamber wall assists in internally reflecting, and thereby propagating the radiant energy waves through the fluid sample analysis chamber. Description of this phenomenon is found in U.S. Pat. Nos. 6,678,051 and 6,734,961, which are assigned to the same assignee in the present application, and which are herein incorporated by reference.

In order to best utilize aqueous fluid samples, therefore, a material having an index of refraction less than that of water is needed to at least form a liner of the fluid analysis chamber wall. One such material is a fluorinated polymer product sold by E.I. du Pont de Nemours and Company of Wilmington, Del. under the trade name Teflon AF®. It is therefore a desired aspect of the fluid analysis cells of the present invention to incorporate a layer of Teflon AF® or other low index of refraction material therewithin to allow efficient radiant energy propagation in spectrophotometry applications.

While various such fluid sample analysis cells and assemblies are currently utilized in the field, certain operational and implementational deficiencies exist. For example, multi-unit flow cell assemblies have found difficulty in being hydraulically sealed to one another when relatively rigid materials such as stainless steel are desired in the fabrication of the bulk cell body parts. In addition, methods for installing radiant energy guiding elements into such flow cells, and particularly those manufactured from stainless steel, have been met with limited success, or are relatively inefficient and expensive to implement.

It is therefore a principal object of the present invention to provide an improved fluid sample analysis apparatus having design features enabling the use of a plurality of distinct metallic cell bodies in fluid connection and hydraulically sealed with one another.

It is another object of the present invention to provide an assembly methodology for installing a radiant energy guiding member into a fluid analysis cell body.

It is a still further object of the present invention to provide an assembly methodology for installing a radiant energy transmitting member into a fluid analysis cell body.

It is a further object of the present invention to provide an outer housing for frictionally securing a multi-unit flow cell assembly in axial alignment therewithin.

SUMMARY OF THE INVENTION

By means of the present invention, an improved fluid sample analysis apparatus is provided for simplifying construction and enhancing the reliability of mounting accuracy of radiant energy guiding members therewithin. Such enhanced accuracy and repeatability of fluid analysis cell construction correspondingly enhances the accuracy achievable in spectrophotometry of fluid samples being analyzed within such cells.

In a particular embodiment, a method for installing a radiant energy transmitting member in a fluid analysis apparatus includes first providing a cell body assembly having an open bore extending at least partially therethrough, with the open bore having first and second opposing open ends. A compressible hollow ferrule is further provided having an inside diameter substantially equal to an outer diameter of the radiant energy transmitting member, and an unstressed outside diameter that is slightly larger than a first diameter dimension of the open bore. The method further includes mounting the ferrule about a first end of the radiant energy transmitting member and inserting a second end of the radiant energy transmitting member into the first end of the open bore to an extent wherein the ferrule is engaged therewithin. The insertion of the ferrule operably causes the ferrule to compress radially inwardly about the radiant energy transmitting member, thereby frictionally engaging and securing the radiant energy transmitting member within the open bore.

The open bore preferably includes a second diameter dimension that is smaller than the first diameter dimension, with the second diameter dimension extending from the second end of the open bore to a position spaced from the first end thereof by a distance at least equal to a length dimension of the ferrule. The juncture of the first and second dimensions of the open bore preferably forms a stop shoulder that operably arrests over-insertion of the ferrule into the open bore.

BRIEF DESCRIPTION OF THE DRAWINGS

FIG. 3 is an isolation side cross-sectional view of a portion of the fluid analysis apparatus illustrated in FIG. 1;

FIG. 4 is an isolation top view of a portion of the fluid analysis apparatus illustrated in FIG. 1;

FIG. 4A is a cross-sectional view taken along cut line 4A-4A in the portion of the fluid analysis apparatus illustrated in FIG. 4;

FIG. 4B is a cross-sectional view taken along cut line 4B-4B in the portion of the fluid analysis apparatus illustrated in FIG. 4;

FIG. 6 is a schematic cross-sectional view of a portion of the fluid analysis apparatus illustrated in FIG. 1 prior to assembly.

FIG. 7 is an isolation top view of a portion of the fluid analysis apparatus illustrated in FIG. 1;

FIG. 8 is a cross-sectional view of a fluid analysis apparatus of the present invention;

FIG. 9 is a cross-sectional view of a fluid analysis apparatus of the present invention.

DETAILED DESCRIPTION OF THE PREFERRED EMBODIMENTS

The objects and advantages enumerated above together with other objects, features, and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

Figure 1:
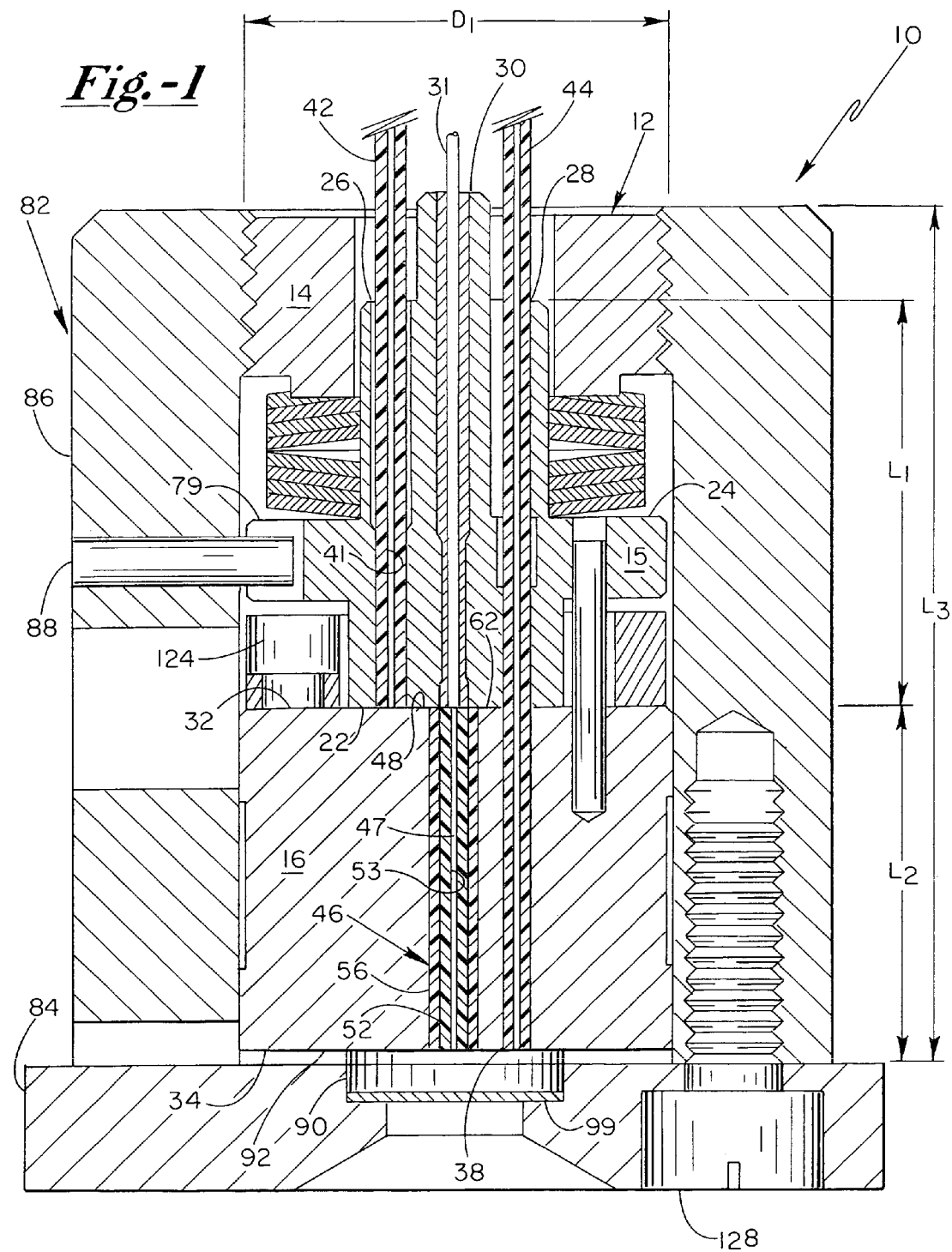
FIG. 1 is an assembly cross-sectional view of a fluid analysis apparatus of the present invention.

With reference now to the drawing figures, and first to FIG. 1, a fluid analysis apparatus 10 of the present invention is shown in cross-section, and includes a cell body assembly 12 having first and second portions 15, 16 which are operably disposed in fluid and optical communication with one another. As illustrated in FIG. 1, first and second portions 15, 16 are preferably mutually independent units that are disposed in axially adjacent relationship with one another.

First portion 15 includes a first end 22 and a substantially opposed second surface 24. In addition, second portion 16 includes a first end 32 and a second substantially opposed end 34, with first end 22 of first portion 15 being operably disposed in facing relationship with first end 32 of second portion 16.

Figure 2:
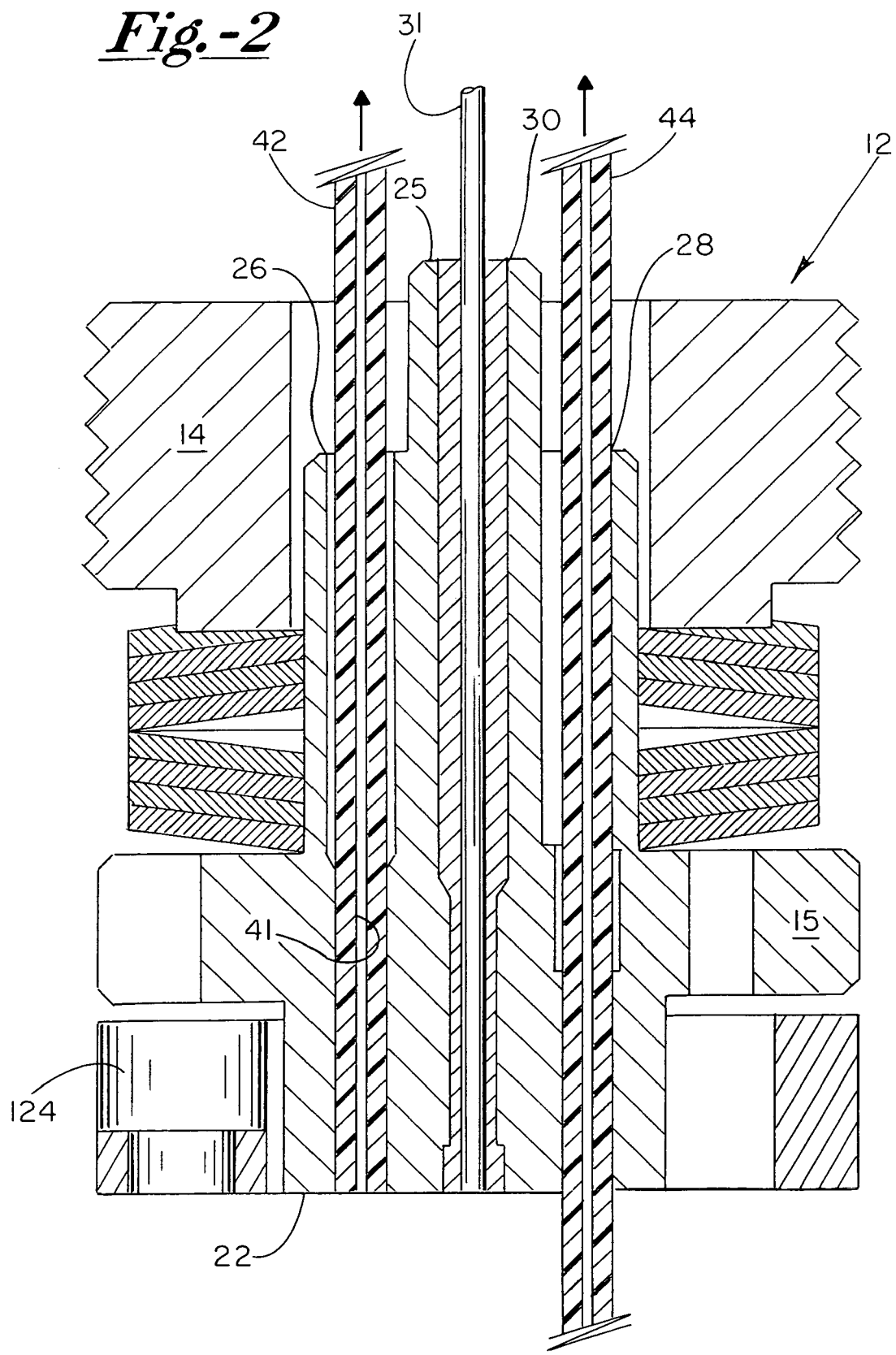
FIG. 2 is an isolation side cross-sectional view of a portion of the fluid analysis apparatus illustrated in FIG. 1.

As best illustrated in the isolation view of FIG. 2, first portion 15 includes an inlet bore 26, a first outlet bore 28, and a radiant energy inlet bore 30. Inlet tube 42 is preferably disposed within inlet bore 26. Such tube 42 is preferably fabricated from an inert material such as PEEK, PTFE, and the like. Inlet tube 42 extends through an axial length "L1" of first portion 15 so as to direct fluid flowing therewithin to first end 22 of first portion 15.

First outlet bore 28 preferably axially extends through length "L1" of first portion 15. Preferably, outlet tube 44 is a unitary piece of tubing extending from second end 34 of second portion 16 through first portion 15 via first outlet bore 28 and second outlet bore 38. Outlet tube 44 is preferably fabricated from an inert material such as PEEK, PTFE, and the like. Inlet tube 42 is preferably compressively friction fit within inlet bore 26 of first portion 15. Outlet tube 44 is preferably compressively friction fit within first outlet bore 28 at second portion 16, while preferably not being friction fit within first outlet bore 28 at first portion 15. Alternatively, however, the frictional fit of inlet and outlet tubes 42, 44 within respective bores of first and second portions 15, 16 may be enhanced through the utilization of adhesives, spot welds, and the like.

Preferably, a radiant energy transmitting member 31 is operably disposed in radiant energy inlet bore 30 of first portion 15. Radiant energy transmitting member 31 is preferably a substantially transparent element that efficiently propagates radiant energy axially therethrough. Accordingly, radiant energy transmitting member 31 is preferably a fiber optic element secured within bore 30 extending axially through first portion 15 from first end 22 through second end 25.

Figure 10:
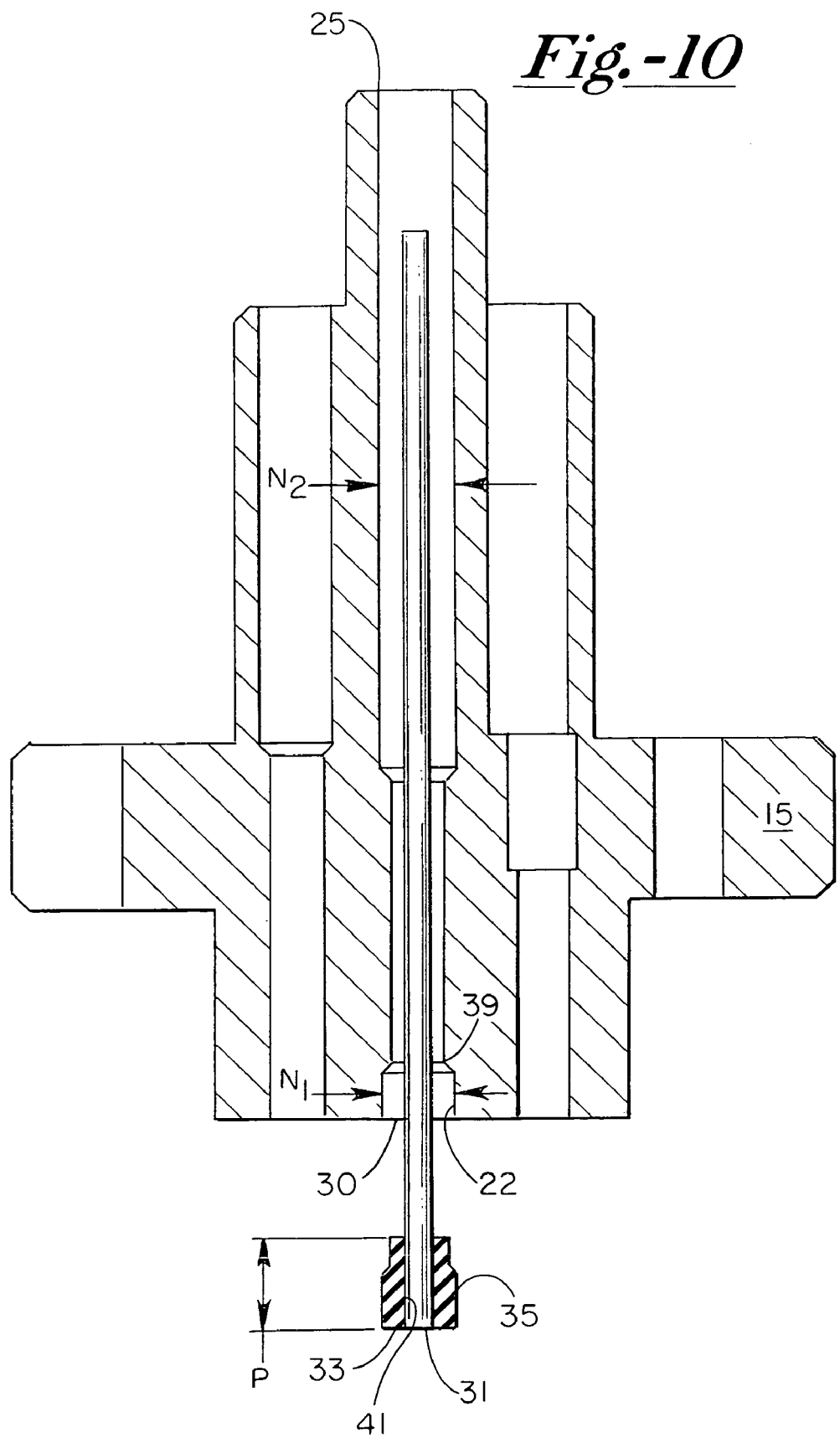
FIG. 10 is an isolation side cross-sectional view of a portion of the fluid analysis apparatus illustrated in FIG. 1, and further showing a preferred installation technique of a radiant energy transmitting member within an open bore of the fluid analysis apparatus.

A preferred method for securing radiant energy transmitting member 31 within bore 30 is illustrated by the apparatus shown in FIG. 10. As shown therein, ferrule 35 is preferably disposed about first end 33 of radiant energy transmitting member 31, with ferrule 35 fitting relatively tightly thereabout. Ferrule 35 is preferably fabricated from a somewhat compressible material, with a particular example being PEEK. In an unstressed condition, ferrule 35 has an outside diameter that is slightly larger than first diameter dimension $N_1$ of bore 30, such that insertion of radiant energy transmitting member 31 with ferrule 35 disposed thereabout causes ferrule 35 to compress radially inwardly about radiant energy transmitting member 31. In doing so, radiant energy transmitting member 31 is frictionally secured within open bore 30.

In order to enable the compressive fitment of ferrule 35 within open bore 30, the outside diameter of ferrule 35 is between about 0.001 and 0.006 inches larger than first inner dimension $N_1$ of bore 30. The compressive action induced upon ferrule 35 through insertion thereof into open bore 30 causes a slight reduction in the inner diameter of ferrule 35 so as to create a tight hydrostatic seal between ferrule 35 and radiant energy transmitting member 31. In preferred embodiments, open bore 30 includes a second diameter dimension $N_2$ that is smaller than first diameter dimension $N_1$, and which extends from second end 25 of open bore 30 to a position spaced from first end 22 thereof by a distance at least equal to a length dimension "P" of ferrule 35, such that full insertion of ferrule 34 into open bore 30 causes end 37 of ferrule 35 to come into contact with stop shoulder 39 formed at the juncture of first and second dimensions $N_1$, $N_2$ of open bore 30. As such, stop shoulder 39 acts to operably arrest over-insertion of ferrule 35 into open bore 30.

In certain embodiments, it is desirable to create an optical finish on end surface 41 of radiant energy transmitting member 31. Such a surface may be created by lapping and polishing any excess material of ferrule 35 and/or radiant energy transmitting member 31 extending out from first end 22 of open bore 30. In embodiments where a pre-finished optical surface 41 of radiant energy transmitting member 31 is provided, ferrule 35 may be pressed flush with respect to first end 22 of open bore 30. Accordingly, the method of the present invention enables a relatively simple technique for installing radiant energy transmitting member 31 into open bore 30 without significant risk of breakage or misalignment thereof.

Conventional methods of installing radiant energy transmitting member 31 into open bore 30 involves the thermal treatment of a polymeric sleeve about radiant energy transmitting member 31 prior to installation. The partially molten sleeve of conventional techniques is then allowed to reform about radiant energy transmitting member 31 subsequent to installation within open bore 30. Such thermal treatment, however, has the negative effect of inducing thermal stresses on radiant energy transmitting member 31, which thermal stresses can result in fractures when lapping and/or polishing procedures are undertaken. Moreover, the use of thermal processing in the prior art prevented the consistent utilization of Teflon AF®-coated fiber optic materials, and instead relied upon polyimide-coated fiber optics, which do not have the desired optical properties of Teflon AF®-coated fiber optic materials.

Radiant energy transmitting member 31 preferably receives radiant energy from a radiant energy source (not shown) and efficiently transmits such radiant energy axially through first portion 15. While a fiber optic element for radiant energy transmitting member 31 is preferred, other radiant energy transmitting materials may be alternatively utilized, as is recognized by those of ordinary skill in the art.

As best illustrated in the isolation view of FIG. 3, second portion 16 preferably includes a second outlet bore 38 that is operably aligned with first outlet bore 28. As such, second outlet bore 38 axially extends through length "L2" of second portion 16. In such a manner, outlet tube 44 axially extends through respective first and second outlet bores 28, 38. In addition, second portion 16 preferably includes a fluid sample analysis chamber 46 which comprises a bore extending axially through second portion 16, and in axial operable alignment with radiant energy inlet bore 30 of first portion 15. In particular, a central axis 47 of fluid sample analysis chamber 46 is preferably substantially coincident with a central axis of the radiant energy inlet bore 30 in first portion 15. As such, radiant energy being transmitted through first portion 15 is delivered to first end 48 of fluid analysis chamber 46.

Preferably, a radiant energy guiding member 52 is axially disposed within the axial bore defining fluid sample analysis chamber 46. As illustrated in FIG. 3, radiant energy guiding member 52 preferably forms a tube radially disposed about central axis 47 of fluid sample analysis chamber 46. In such a manner, radiant energy guiding member 52 concentrically surrounds an axis of radiant energy travel through radiant energy transmitting member 31 and through fluid sample analysis chamber 46, as defined by central axis 47. Radiant energy, therefore, is allowed to enter fluid sample analysis chamber 46 in a zone defined by inner diameter 53 of radiant energy guiding member 52.

As described hereinabove, radiant energy guiding member 52 is preferably fabricated from a material selected for its optical properties, and specifically for radiant energy propagation characteristics. In applications such as those contemplated by the present invention wherein radiant energy is being operably propagated through a fluid field, it is desirable that the material forming the channel wall confining the fluid sample and radiant energy has an index of refraction less than that of the fluid sample being analyzed. Since, in certain applications, the fluid sample being analyzed by the apparatus of the present invention may be aqueous, radiant energy guiding member 52 is preferably fabricated from a material having index of refraction less than that of water. A particularly preferred example of such a material is a fluorinated polymer product manufactured and sold by E.I. du Pont de Nemours and Company under the trade name Teflon AF® 2400. Applicants have determined that a radiant energy guiding member 52 being fabricated from Teflon AF® 2400 provides desired radiant energy propagation characteristics in the apparatus of the present invention. Accordingly, radiant energy guiding member 52 may take the form of a tube radially disposed about central axis 47 and fabricated from Teflon AF® 2400.

In some embodiments of the present invention, radiant energy guiding member 52 is at least partially coaxially contained within a sleeve member 56, which sleeve member 56 assists in centrally aligning radiant energy guiding member 52 within the bore defining fluid sample analysis chamber 46, as well as inserting radiant energy guiding member 52 into fluid sample analysis chamber 46. Preferably, sleeve member 56 is fabricated a relatively resilient polymeric material such as TEFZEL®, FEP, or PTFE. TEFZEL® is available from E.I. du Pont de Nemours and Company of Wilmington, Del.

As noted above, radiant energy guiding member 52 preferably acts to propagate radiant energy through an internal channel defined by inner wall 53 thereof. Materials which are currently commercially available for use in radiant energy guiding member 52 are typically substantially transparent. Thus, radiant energy impinging upon, for example, first end 48 of radiant energy guiding member 52 may pass axially through a sidewall of radiant energy guiding member 52 to second end 50 thereof. The passage of such radiant energy is considered "stray light", which can detrimentally affect the accuracy of spectrophoresis fluid analysis due to the fact that a certain portion of the radiant energy passing through fluid sample analysis chamber 46 has not passed through the fluid sample being analyzed. Accordingly, it is an important aspect of the fluid sample analysis chamber 46 of the present invention to effectively mask or otherwise prevent radiant energy from passing through fluid sample analysis chamber 46 without first passing through the fluid sample being analyzed. One method of masking such stray light is in fabricating and installing a physical masking element that is placed at first end 48 of fluid sample analysis chamber 46, with such masking element having an aperture disposed therein, and which aperture is operably aligned with the open channel defined by radiant energy guiding member 52, such that radiant energy is not allowed to enter into the sidewall of radiant energy guiding member 52. Another method for effectively preventing the transmission of stray light through fluid sample analysis chamber 46 is to render opaque at least a portion of radiant energy guiding member 52 and sleeve member 56. A method for blocking stray light through the use of an opaque radiant energy guiding member 52 is described in U.S. Pat. No. 6,734,961, which is assigned to the same assignee as in the present invention, and the contents of which are incorporated herein by reference.

With reference back to FIG. 1, fluid analysis apparatus 10 preferably further includes a first resilient gasket 62 interposed between respective first ends 22, 32 of first and second portions 15, 16 of cell body assembly 12. Resilient gasket 62 preferably acts to fluidly couple and hydraulically seal first and second portions 15, 16 to one another. As best illustrated in the isolation top view of FIG. 4, resilient gasket 62 includes a first radiant energy aperture 64 that is mounted in fluid analysis apparatus 10 in operable alignment with radiant energy inlet bore 30 and fluid sample analysis chamber 46, and more particularly in operable alignment with radiant energy transmitting member 31 and the central channel defined by inner wall 53 of radiant energy guiding member 52. As such, radiant energy is allowed to pass through aperture 64 from radiant energy transmitting member 31 to within a channel defined by radiant energy guiding member 52. As described above, a particular aspect of the present invention is to prevent and otherwise mask radiant energy being delivered by radiant energy transmitting member 31 to enter into the sidewall of radiant energy guiding member 52. As such, first radiant energy aperture 64 in resilient gasket 62 may be of a dimensional tolerance allowing for a substantial diametrical match between first radiant energy aperture 64 and the channel defined by radiant energy guiding member 52. In such an embodiment, resilient gasket 62 is preferably fabricated from a substantially opaque material. Since alignment of resilient gasket 62 with fluid analysis apparatus 10 may be difficult where the diametrical size of first radiant energy aperture 64 is substantially equal to the channel defined by radiant energy guiding member 52, certain embodiments of the present invention provide for a first radiant energy aperture 64 having a diameter somewhat greater than the diameter of the channel defined by radiant energy guiding member 52, particularly where radiant energy guiding member 52 is made opaque in accordance with U.S. Pat. No. 6,734,961 referenced above so as not to permit passage of radiant energy through the sidewall of guiding member 52.

Resilient gasket 62 preferably further includes a second fluid sample outlet aperture 66 that is preferably installed in fluid analysis apparatus 10 in operable alignment with respective first and second outlet bores 28, 38 of first and second portions 15, 16. As such, fluid sample outlet tube 44 preferably extends through second fluid sample outlet aperture 66 of first resilient gasket 62. As a consequence of fluid sample outlet tube 44 being unitary, the diametrical dimension of second fluid sample outlet aperture 66 may be larger than the respective diameters of the first and second fluid outlet bores 28, 38. In fact, it is a preferred aspect of the present invention to provide second fluid sample outlet aperture 66 with a diameter substantially greater than first and second outlet bores 28, 38 so as to facilitate placement and alignment of first resilient gasket 62 within fluid analysis apparatus 10. Second fluid sample aperture 66 is preferably at least about 0.010 inches in diameter, and more preferably between about 0.010 and 0.060 inches in diameter.

As illustrated in FIG. 4, first resilient gasket 62 preferably further includes a fluid sample transfer groove 68 extending from a fluid sample inlet portion 70 to first radiant energy aperture 64. Fluid sample inlet portion 70 of first resilient gasket 62 is preferably installed in fluid analysis apparatus 10 in operable alignment with inlet bore 26 of first portion 15, and particularly in alignment with inlet tube 42 extending through inlet bore 26. As a result, fluid sample exiting from inlet tube 42 at first end 22 of first portion 15 is directed toward and to first radiant energy aperture 64 via fluid sample transfer groove 68. Inlet sample fluid then enters into fluid sample analysis chamber 46 through radiant energy aperture 64 of resilient gasket 62.

In preferred embodiments of the present invention, fluid sample transfer groove 68 extends only partially through a thickness dimension of first resilient gasket 62, as illustrated in the cross-sectional end view of FIG. 4A. One purpose for extending groove 68 only partially through thickness dimension "T" of resilient gasket 62 is to maintain the opacity of resilient gasket 62 at all locations except for apertures 64 and 66, such that incoming radiant energy passing from radiant energy transmitting member 31 does not leak into the sidewall of radiant energy guiding member 52. In embodiments utilizing an opaque radiant energy guiding member 52, however, fluid sample transfer groove 68 extends completely through a thickness dimension "T" of first resilient gasket 62. Moreover, fluid sample inlet portion 70 may extend either partially or fully through thickness dimension "T" of first resilient gasket 62 as desired per application.

In particularly preferred embodiments of the present invention, first and second portions 15, 16 of cell body assembly 12 are fabricated from an inert metallic material such as stainless steel. A deficiency in conventional fluid analysis systems that is addressed by the present invention is in the hydraulic sealing of distinct metallic components to one another, such as in the hydraulic sealing of first and second portions 15, 16 of cell body assembly 12. Conventional designs are unable to hydraulically seal metallic components such as first and second portions 15, 16 to one another in order to prevent fluid leakage when operating under relatively high internal fluid pressures. First resilient gasket 62, however, enables the hydraulic sealing of first and second portions 15, 16 to one another to a sufficient degree so as to maintain a hydraulic seal even under relatively high contemplated operating fluid pressures. In a like manner, second resilient gasket 92 enables the hydraulic sealing of second portion 16 to cell window 96. In order to enable such a hydraulic seal, gasket 62 is preferably fabricated from a resilient and compliant material, but which maintains its structural integrity and operational alignment characteristics when press-fit between first and second portions 14, 16. Example materials useful in gaskets 62 and 92 of the present invention include Kapton® or coated metal substrates, such as stainless steel metal substrates coated on one or both major surfaces 71, 72 with a resilient material such as PTFE or fluorourethane. Fluorourethane useful in topical coating applications of gaskets 62, 92 of the present invention are available from 21$^{st}$ Century Coatings of Vancouver, British Columbia, or by direct synthesis as described in "Fluoropolymers 1, Synthesis" by Hougham et al. 1999.

Gasket 62 is preferably about 50 μm in thickness dimension "T". In embodiments wherein gasket 62 is a coated metal substrate, the metal substrate is about 50 μm thick, while the resilient material coating is between about 1 and 40 μm thick on each major surface 71, 72.

Where first or second gaskets 62, 92 are fabricated from non-opaque materials, or materials that do not render the finished gasket opaque due to the relatively small thickness thereof, radiant energy aperture 64 may preferably include, for example, a metalized coating radially disposed about a circumference thereof. Such a metalized coating preferably radially extends about aperture 64 to an extent sufficient to block stray light entering the sidewall of radiant energy guiding member 52. As such, the metalized coating extends between about 100 and 500 μm beyond an outer circumferential dimension of aperture 64. Alternatively, opaque coatings of non-metallic materials may be disposed about the perimeter of aperture 64. Such opaque coatings, however, are not necessary where radiant energy guiding member 52 includes a radiant energy blocking opaque portion, as described above.

In a particular aspect of the present invention, the thickness dimension "T" of gaskets 62, 92 result in a known transfer zone length 65 of aperture 64 through which the sample fluid and radiant energy concurrently travel. In operation, sample fluid fills aperture 64 throughout transfer zone length 65, thereby resulting in calculatable radiant energy losses as the radiant energy passes through the fluid-filled transfer zone 65 which is absent radiant energy guiding member 52. As a result, radiant energy entering aperture 64 is allowed to disperse throughout the volume defined by transfer zone 65, causing partial diffusion or loss of the radiant energy. Fluids having relatively higher refractive indexes result in a greater degree of radiant energy loss in transfer zone 65 as compared to fluids having relatively lower refractive indexes. This relationship is described in U.S. Pat. No. 6,678,051, which is assigned to the same assignee as in the present application, and is incorporated herein by reference.

Using such a relationship, a fabricator of cell body assembly 12 of the present invention may select an appropriate thickness dimension "T" for one or more of first and second gaskets 62, 92 to thereby define a desired transfer zone dimension 65 which corresponds to a calculatable amount of radiant energy loss in passing through aperture 64. Such a controllable variable allows the fabricator to install one or more gaskets 62, 92 of known thickness dimension "T" that effectively calibrate energy losses through apparatus 10 when utilized in connection with various fluids having different indexes of refraction. In such a manner, radiant energy losses through apparatus 10 may be standardized for use with various fluids by assigning gaskets 62, 92 of appropriate calibrating thickness, "T".

For example, a relatively high refractive index fluid being operably disposed within aperture 64 is preferably utilized in combination with one or more gaskets, 62, 92 having a relatively smaller thickness dimension "T" to offset the relatively higher degree of radiant energy loss caused by the relatively high refractive index fluid. Correspondingly, a relatively larger thickness dimension "T" for gasket 62, 92 may be employed where a relatively lower refractive index fluid is being utilized in apparatus 10. Through such a methodology, unique gasket combinations may be utilized as appropriate for the respective fluid being operably exposed to the radiant energy transmitted through apparatus 10.

With reference back to FIG. 1, fluid analysis apparatus 10 preferably includes an outer housing 82 having a first base portion 84 and a substantially cylindrical sidewall 86 extending from base portion 84 so as to at least partially concentrically enclose cell body assembly 12 within a boundary defined by the combination of base portion 84 and sidewall 86. Preferably, inner diameter "$D_1$" of sidewall 86 is specifically dimensioned to allow first and second portions 15, 16 to be inserted into the chamber defined by base portion 84 and sidewall 86 with a circumferential clearance of between about 5 and 20 µm. It has been determined by the Applicants that an operational advantage of accurate axial alignment among a plurality of distinct units making up cell body assembly 12 is facilitated through the incorporation of a distinct outer housing unit 82. As such, at least first and second portions 15, 16 are accurately axially aligned with one another simply by installing such first and second portions 15, 16 within the at least partial confines of outer housing 82.

In the past, inefficient manual alignment of multiple distinct parts making up cell body assembly 12 was required in order to insure correct axial alignment among such distinct elements making up cell body assemblies 12. Outer housing 82 of the present invention eliminates this inefficient procedure by preparing a compartment of predetermined dimensions which closely secures cell body 12 therewithin. Such a utility is particularly applicable in cell body assemblies 12 having relatively longer total length "L3" dimensions. Preferably, cell body assembly 12, including nut 14, has a total length "L3" of between about 2 and about 100 mm, with particularly preferred embodiments of cell body assembly 12 being 3, 5, 10, 25, and 75 mm in total length "L3".

In some embodiments of the present invention, outer housing 82 includes an anti-rotation member 88 disposed in sidewall 86 for operable engagement with a correspondingly-configured notch 79 in first portion 15. Such notch 79, however, may instead be located in second portion 16. Moreover, more than one anti-rotation member/notch combinations may be incorporated into fluid analysis apparatus 10 of the present invention.

As further illustrated in FIG. 1, a second resilient gasket 92 is preferably interposed between second end 34 of second portion 16 and base portion 84 of outer housing 82. Second resilient gasket 92 may preferably be identical to first resilient gasket 62, but with fluid sample inlet portion 70 of first resilient gasket 62 acting as a second fluid sample outlet portion in second resilient gasket 92. Accordingly, fluid sample inlet portion 70 may comprise an aperture extending through thickness dimension "T" for purposes of second resilient gasket 92. As so configured, second fluid sample outlet aperture 70 of second resilient gasket 92 is installed in fluid analysis apparatus 10 in operable alignment with second outlet bore 38 of second portion 16. In such a manner, fluid sample exiting from fluid sample analysis chamber 46 is directed into second outlet bore 38, and particularly into fluid sample outlet tube 44 via second fluid sample outlet aperture 70 in second resilient gasket 92.

Second resilient gasket 92 is preferably provided at second end 34 of second portion 16 so as to provide a hydraulic seal between second portion 16 and a window 96 disposed in base portion 84 of outer housing 82. As is known in the art, window 96 may be fabricated from, for example, fused silica, diamond, sapphire, or other inert materials transparent to the radiant energy wavelength being utilized in apparatus 10, and is utilized to transmit radiant energy exiting from fluid sample analysis chamber 46 to a radiant energy detector (not shown). Second resilient gasket 92 is preferably fabricated from materials as described above with reference to first resilient gasket 62. Moreover, second resilient gasket 92 is preferably oriented such that transfer groove 68 is in operable facing relationship with window 96, thereby reducing fluidically unswept volume.

Preferably, a third gasket 99 is operably disposed between window 96 and base portion 84 to thereby assist in ensuring proper alignment between second surface 34 of second portion 16 and window 96. Third gasket 99 is illustrated in FIG. 7 as having an aperture 101 of a dimension large enough to avoid blockage or interference of radiant energy exiting from window 96 through base portion 84. Third gasket 99 is preferably fabricated from a resilient material that operably compresses between window 96 and base portion 84 when pressure is applied to window 96 from second portion 16 as a result of nut 14 driving first and second portions 15, 16 toward base portion 84. Such a compressible third gasket 99 assists in allowing respective substantially planar surfaces, as between window 96 and second surface 34 of second portion 16 to become parallely aligned with one another through the axial mounting of second portion 16 against window 96 via the tightening of nut 14 within outer body 82. Most preferably, third gasket 99 is fabricated from a transparent inert material such as FEP, TEFZEL®, or the like.

Figure 5:
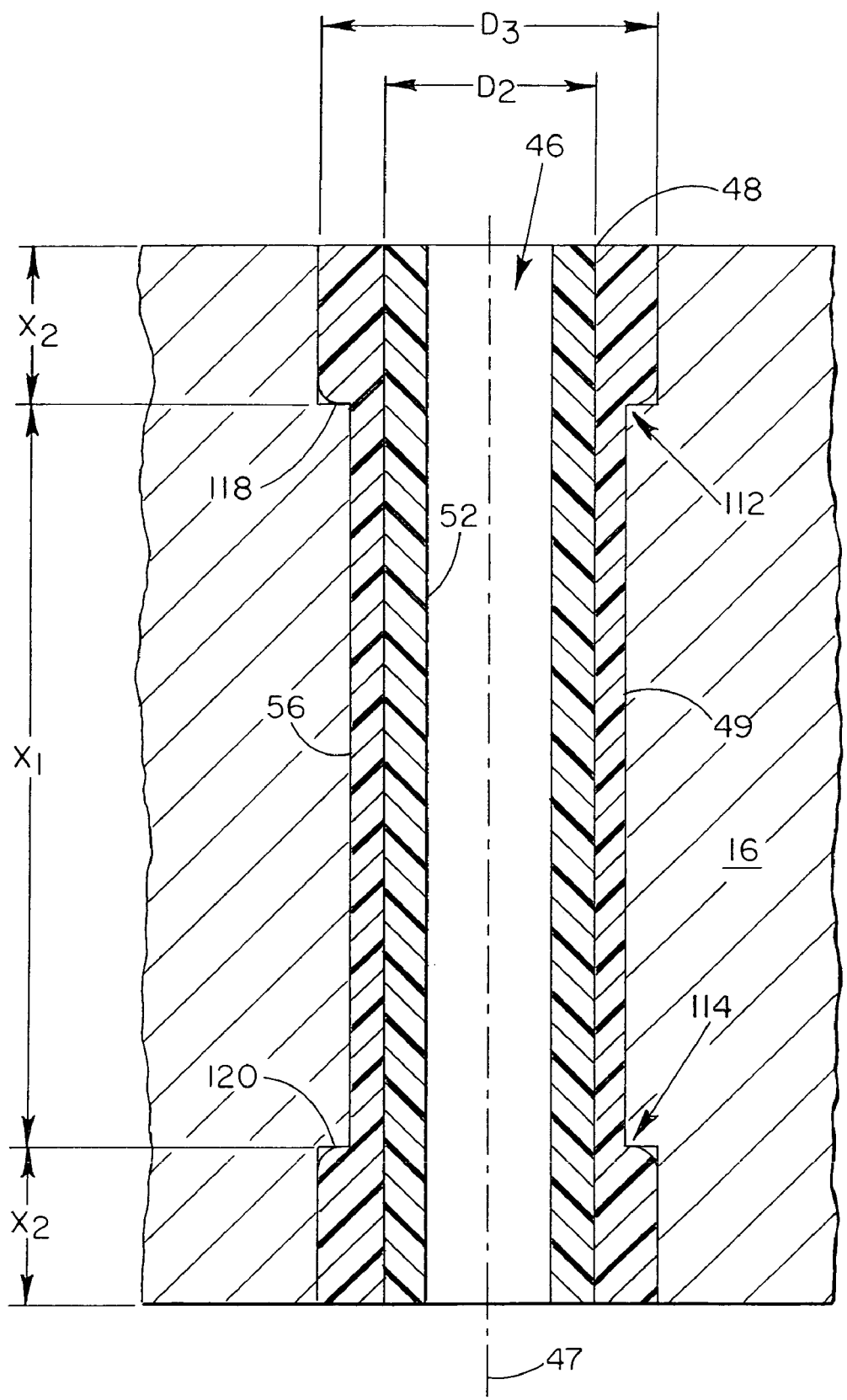
FIG. 5 is an enlarged cross-sectional view of a portion of the fluid analysis apparatus illustrated in FIG. 1.

In the embodiment of second portion 16 illustrated in FIG. 5, a first locking structure 112 is provided at fluid sample analysis chamber 46, and disposed adjacent to first end 48 of fluid sample analysis chamber 46. First locking structure 112 is preferably a design detail of second portion 16 of cell body assembly 12, and is specifically configured to operably and statically secure radiant energy guiding member 52 within fluid sample analysis chamber 46. First locking structure 112 acts to operably inhibit relative motion between the combination of radiant energy guiding member 52 and sleeve member 56 with respect to second portion 16.

Such resistance to movement is developed through only the frictional resistance forces developed at the interface between first locking structure 112 and sleeve member 56, due to the fact that sleeve member 56 is securely compressively fit in fluid sample analysis chamber 46 against chamber wall 49. In addition, radiant energy guiding member 52 is frictionally secured to sleeve member 56 through a process described hereinbelow. First locking structure 112, therefore, provides a focal point for generating a relatively large degree of frictional resistance to relative motion between sleeve member 56 and second portion 16, thereby lockably retaining radiant energy guiding member 52 within fluid sample analysis chamber 46.

Preferably, fluid sample analysis chamber 46 includes a first diameter dimension $D_2$ extending through a first length $x_1$ of fluid sample analysis chamber 46 and a second diameter dimension $D_3$ extending through a second length $x_2$ of fluid sample analysis chamber 46. As illustrated in FIG. 5, second diameter dimension $D_3$ is preferably somewhat larger than first diameter dimension $D_2$ by an amount sufficient to provide first locking structure 112 with an adequate focal point of frictional resistance to relative motion between sleeve member 56 and second portion 16. Preferably, second diameter dimension $D_3$ is larger than first diameter dimension $D_2$ by about 0.001 inches, with first diameter dimension $D_2$ being about 0.03 inches. The change in diameter dimension of fluid sample analysis chamber 46 at first locking structure 112 forms a first transition segment 118 that is preferably angularly oriented to chamber wall 49.

As shown in FIG. 5, second portion 16 may additionally include a second locking structure 114 having a second transition segment 120 formed therewith. The embodiment illustrated in FIG. 5 is representative of a variety of configurations for first and second locking structures 112, 114. For example, first and second transition segments 118, 120 may alternatively reflect a different configuration altogether. In addition, second diameter dimension $D_3$ may alternatively be smaller than first diameter dimension $D_2$, or may be alternated among first and second locking structures 112, 114. Furthermore, one or more of such locking structures 112, 114 may be incorporated into the apparatus of present invention while remaining within the scope contemplated by the Applicants. The embodiments shown and described herein merely represent examples of internal alterations in diameter dimension of fluid sample analysis chamber 46 so as to create one or more foci of frictional resistance between sleeve member 56 and chamber wall 49.

A preferred method for securely installing radiant energy guiding member 52 within fluid sample analysis chamber 46 includes a sleeved compression technique that utilizes the resilient nature of sleeve member 56. Sleeve member 56, as described above, is preferably fabricated from a relatively resilient material such as TEFZEL® or the like, and is shaped as a tube having an unstressed outer diameter that is slightly larger than second diameter dimension $D_3$ of fluid sample analysis chamber 46, and an inner diameter dimension that is substantially equal to but slightly larger than an outer diameter of radiant energy guiding member 52. Initially, radiant energy guiding member 52 is inserted into the channel defined by sleeve member 56, as is illustrated in FIG. 6. Sleeve member 56 is preferably initially somewhat longer than radiant energy guiding member 52 so as to provide a location at second end 51 for grasping and pulling sleeve member 56 into and through fluid sample analysis chamber 46.

Sleeve member 56 is preferably operably elongated along direction "Y", which elongation reduces both the inner and outer diameter of sleeve member 56 so as to be small enough to be fed through fluid sample analysis chamber 46. Such diameter reduction of sleeve member 56 further acts to tightly frictionally engage radiant energy guiding member 52 therewithin. However, the elastic limit of sleeve member 56 should not be exceeded during the installation procedure. Once the combination of sleeve number 56 and radiant energy guiding member 52 are in place within fluid sample analysis chamber 46, the combination is allowed to relax under its inherent resilient restorative forces to thereby frictionally engage and secure sleeve member 56 to chamber wall 49.

To further enhance and assist the physical relaxation of sleeve number 56 and radiant energy guiding member 52 into the configuration illustrated in FIG. 5, one or more thermal treatment cycles are conducted on the installed combination of sleeve member 56 and radiant energy guiding member 52 within second portion 16. A thermal cycle represents elevating the temperature environment surrounding the combination to between about 80 and 100 degrees Celsius for a period of about 10 minutes. Though the ramp up and ramp down rates are not overly critical to the thermal cycle performance, it has been found that a preferred temperature ramp up rate of 10 degrees Celsius per minute, and a ramp down rate of 20 degrees Celsius per minute is preferred. In a particular embodiment of the invention, 4 cycles between ambient temperature and a maximum thermal treatment temperature of about 80 degrees Celsius are preformed on the combination to fully relax sleeve member 56 and radiant energy guiding member 52 into frictional engagement with chamber wall 49 consistent with the configuration illustrated in FIG. 5. Once the thermal cycles are complete, excess material extending out from fluid sample analysis chamber 46 is cleaved using, for example, a microtoming procedure.

When radiant energy guiding member 52 is left as a substantially transparent body, sleeve member 56 may also be manufactured using semitransparent materials, as first gasket 62 is, in such embodiments, is configured to mask all stray light from entering both sleeve member 56 and light guiding member 52. In the circumstance where in radiant energy guiding member 52 is rendered opaque as described above, first gasket 62 need not mask stray light, so long as sleeve member 56 is also fabricated from opaque materials. In embodiments wherein both sleeve member 56 and radiant energy guiding member 52 are opaque to an extent necessary to prevent passage of stray light therethrough, first gasket 62 is merely required to serve as a fluid directing element, a spacing element, and a compliant sealing element between adjacent portions of cell body assembly 12.

In another embodiment of the present invention, and as illustrated in FIG. 8, apparatus 210 includes a cell body assembly 212 operably disposed within outer body 282. Nut 214 is preferably threadably insertable within outer body 282, and operably presses against spring washers 213 in order to tightly install first, second, and third portions 215, 216, 217 within outer body 282. As shown in FIG. 8, cell body assembly 212 includes first portion 215, a second portion 216, and third portion 217. First portion 215 includes an inlet bore 226 in which inlet tubing 242 is operably disposed, but does not incorporate a first outlet bore as described with reference to numeral 28 in first portion 15 of apparatus 10. Instead, third portion 217 includes a fluid outlet bore 229 and outlet tubing 233 for operably enabling the removal of sample fluid from apparatus 210. Due to the inclusion of outlet bore 229 and outlet tubing 233 in third portion 217, second portion 216 preferably does not include an outlet bore disposed therein as described with reference to first outlet bore 38 in apparatus 10.

Third portion 217 preferably further includes a radiant energy outlet bore 281 in which a fiber optic element 282 is operably disposed for transmitting radiant energy from fluid analysis chamber 246 to a radiant energy detector (not shown). In the embodiment illustrated in FIG. 8, therefore, third portion 217 replaces window 96 of apparatus 10 in transmitting radiant energy out from apparatus 210. Furthermore, cell body assembly 212 preferably utilizes first and second resilient gaskets 262, 292 as described above with reference to first and second resilient gaskets 62, 92. However, second resilient gasket 292 is preferably oriented to align transfer groove 268 between fluid analysis chamber 246 and outlet bore 229 of third portion 217, such that fluid exiting fluid analysis chamber 246 is operably directed to outlet tubing 233. A further aspect of the embodiment illustrated in FIG. 8 is that both first and third portions 215, 217 may be manufactured as substantially identically components, and need only be positioned within apparatus 210 in a reverse orientation with respect to one another in order to effectuate input and withdrawal of both fluid sample and radiant energy into and out from cell body assembly 212.

A further embodiment of the present invention is illustrated in FIG. 9, wherein apparatus 310 includes a first portion 315 as described above with reference to first portion 15 of apparatus 10, a second portion 316 configured in accordance with second portion 16 of apparatus 10, and first and second resilient gaskets 362, 392 fabricated and configured in accordance with first and second resilient gaskets 62, 92 of apparatus 10. However, apparatus 310 preferably includes a third portion 317 functionally positioned in place of window 96 of apparatus 10, wherein third portion 317 includes a radiant energy outlet bore 381 having an outlet radiant energy transmitting member 383 disposed therein for operably transmitting radiant energy from fluid analysis chamber 346 to a radiant energy detector (not shown). Third portion 317 is preferably hydraulically sealed to second portion 316 through a compression fit with second resilient gasket 392 disposed therebetween.

With reference back to FIG. 1, cell body assembly 12 is preferably radially secured in place by outer housing 82. However, the plurality of distinct portions, such as first and second portions 15, 16 of cell body assembly 12 may additionally require fasteners, such as nut 14 for axially coupling first and second distinct portions 15, 16 to one another. Other means of securing respective components of cell body assembly 12 in place include, for example, clamping devices, adhesives, and the like. As is further illustrated in FIG. 1, base portion 84 is preferably operably secured to sidewall 86 of outer housing 82 via screws 128.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A method for installing a radiant energy transmitting member in a fluid analysis apparatus for containing and analyzing a fluid sample, the method comprising the steps of:
    (a) providing a cell body assembly having an open bore extending at least partially therethrough, said open bore having first and second opposing open ends;
    (b) providing a compressible hollow ferrule having an inside diameter substantially equal to an outer diameter of said radiant energy transmitting member, and an unstressed outside diameter that is slightly larger than a first diameter dimension of said open bore;
    (c) mounting said ferrule about a first end of said radiant energy transmitting member; and
    (d) inserting a second end of said radiant energy transmitting member into said first end of said open bore to an extent wherein said ferrule is engaged therewithin, such insertion of said ferrule operably causing said ferrule to compress radially inwardly about said radiant energy transmitting member, thereby frictionally engaging and securing said radiant energy transmitting member within said open bore.

2. A method as in claim 1 wherein said radiant energy transmitting member is a fiber optic material.

3. A method as in claim 1 wherein said ferrule is fabricated from PEEK.

4. A method as in claim 1 wherein said open bore includes a second diameter dimension that is smaller than said first diameter dimension, said second diameter dimension extending from said second end of said open bore to a position spaced from said first end thereof by a distance at least equal to a length dimension of said ferrule.

5. A method as in claim 4 wherein the juncture of said first and second dimensions of said open bore forms a stop shoulder that operably arrests over-insertion of said ferrule into said open bore.

* * * * *